United States Patent [19]

Spademan

[11] Patent Number: 5,092,321
[45] Date of Patent: Mar. 3, 1992

[54] WALKER BRACE

[76] Inventor: Richard G. Spademan, 2600 Capitol Ave., Sacramento, Calif. 95816

[21] Appl. No.: 638,519

[22] Filed: Jan. 3, 1990

Related U.S. Application Data

[63] Continuation-in-part of Ser. No. 408,653, Sep. 18, 1989.

[51] Int. Cl.[5] .......................... A61F 5/04; A61F 5/14
[52] U.S. Cl. .................................. 602/27; 128/599; 602/16
[58] Field of Search .................. 128/84 R, 83, 83.5, 128/88, 80 H, 80 R, 80 F, 84 C, 80 DB, 80 D, 80 C, 87 R, 166, 599

[56] References Cited

U.S. PATENT DOCUMENTS

| | | | |
|---|---|---|---|
| 2,206,234 | 7/1940 | Murray | 128/83.5 |
| 2,512,826 | 6/1950 | Clark | 128/80 F |
| 2,516,872 | 8/1950 | Hauser | 128/80 H |
| 2,525,658 | 10/1950 | Dumelin | 128/80 H |
| 2,591,373 | 4/1952 | Petruch | 128/80 F |
| 2,594,227 | 4/1952 | Smith | 128/80 F |
| 2,883,982 | 4/1959 | Rainey | 128/80 F |
| 3,481,332 | 12/1969 | Arnold | 128/80 R |
| 4,771,768 | 9/1988 | Crispin | 128/88 |
| 4,856,500 | 8/1989 | Spademan | 128/88 |

Primary Examiner—Robert A. Hafer
Assistant Examiner—Michael Brown
Attorney, Agent, or Firm—Townsend and Townsend

[57] ABSTRACT

A walker brace for temporary tightening from a close fit position during the support surface contact phase of gait when the patient's weight is applied to the sole to stabilize the leg, ankle and foot from undesirable movement. In a preferred embodiment, a leg support assembly (2) of the brace has multiple straps (15, 16) connected to an arm (4) for nesting the leg. A foot support assembly (3) has multiple straps (31, 32) connected to a foot support shell (28) for nesting the foot. An arm (5) is connected to the foot support shell (28) and articulates relative to the arm (4) at a controlled motion ankle hinge (6). A leg strap tightening mechanism (18) includes a tightening rod (20) and a cable (22) for progressive and differential tightening of the straps (15, 16) to stabilize the leg. A foot strap tightening mechanism (44) includes a buckle loop (34) and a cable (41) for tightening of the instep strap (32) to stabilize the foot. The cables (22, 41) pass through foot support shell (28) and a rocker bottom sole shell (29) pivoted at the foot support shell (28). A relative shortening of the cables (22, 41) occurs when the rocker bottom sole shell (29) is pivoted upwardly relative to the foot support shell (28) during the period of time that the patient's weight is applied to the sole.

18 Claims, 4 Drawing Sheets

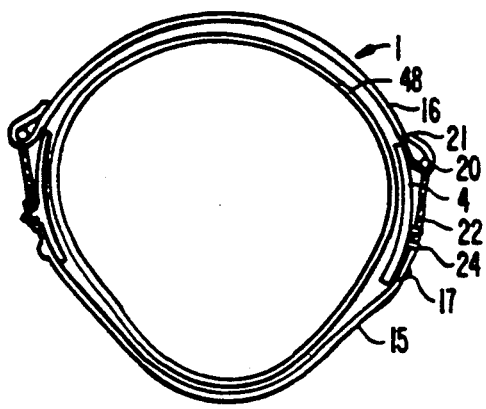
FIG._2.
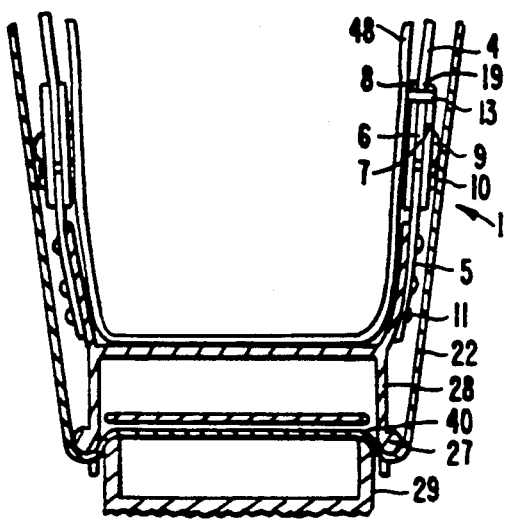
FIG._3.
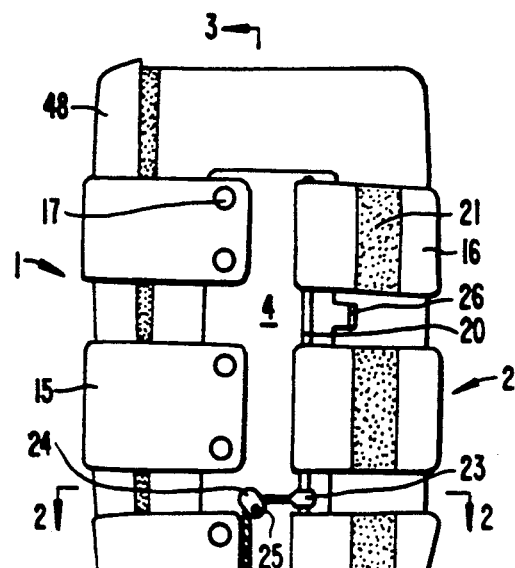
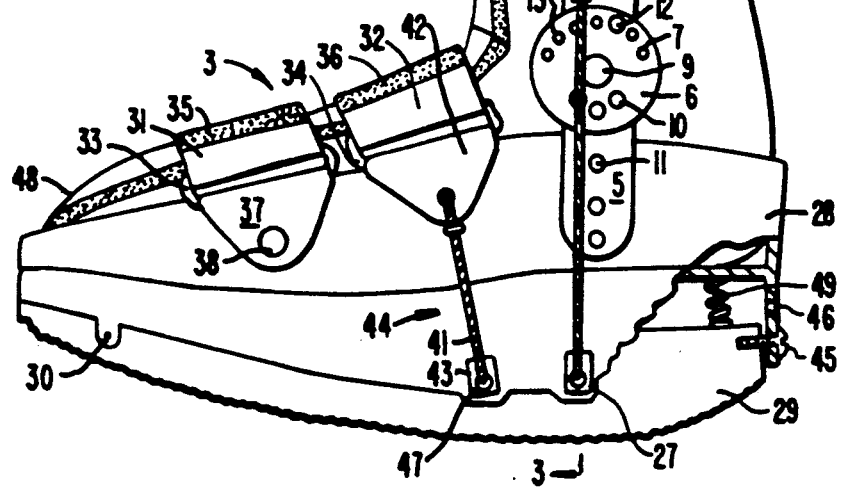
FIG._1.

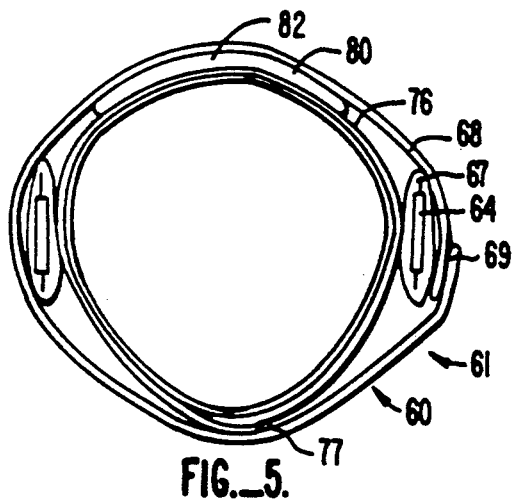
FIG._5.
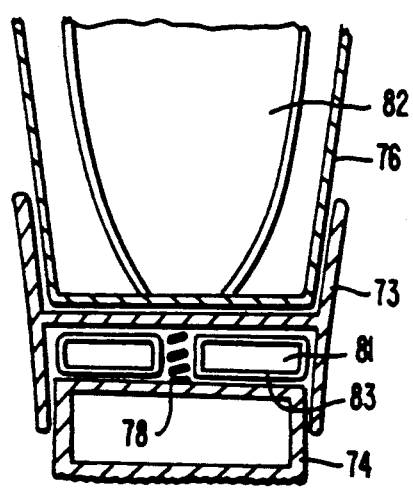
FIG._6.
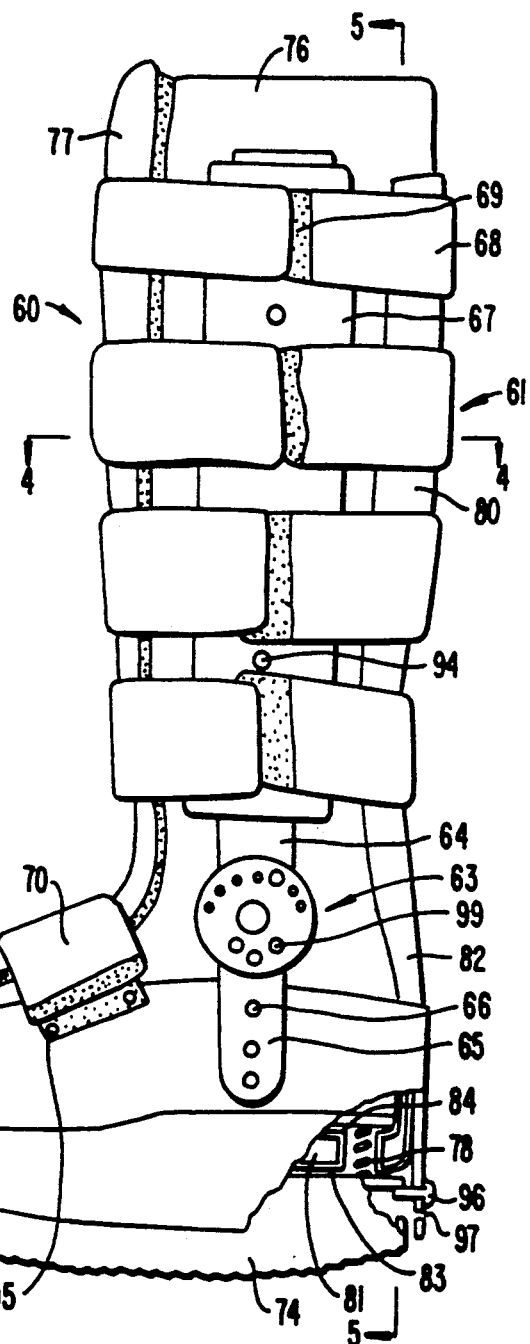
FIG._4.

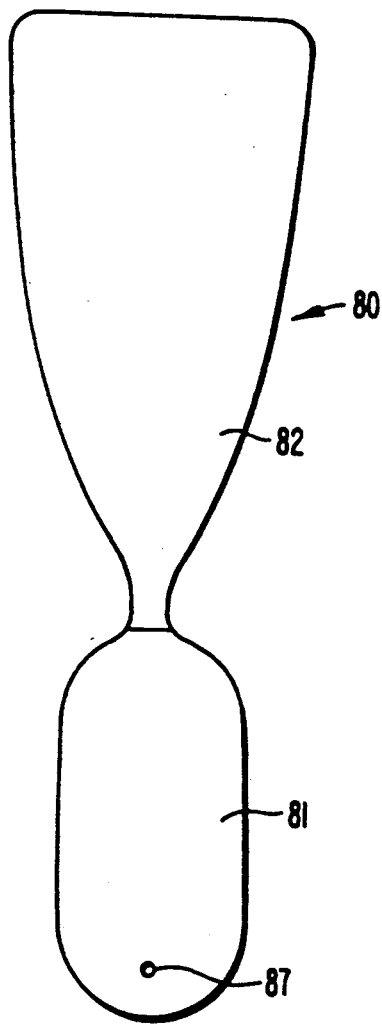
FIG._7.
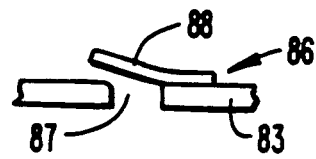
FIG._8.
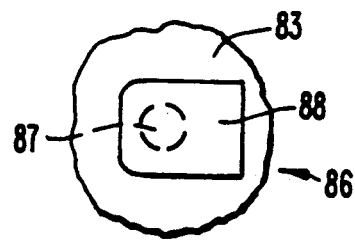
FIG._9.
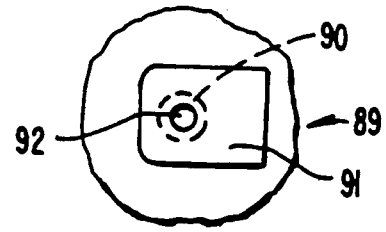
FIG._11.
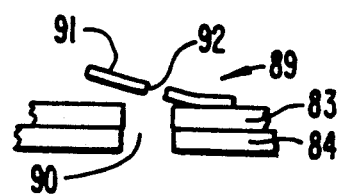
FIG._10.

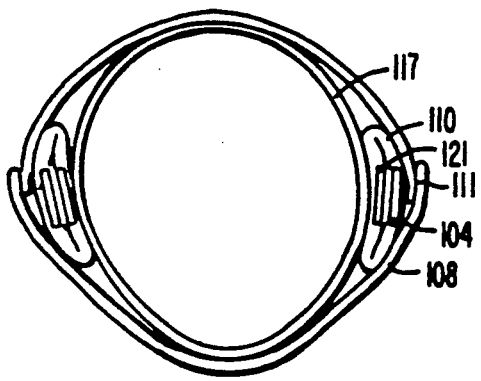
FIG._13.
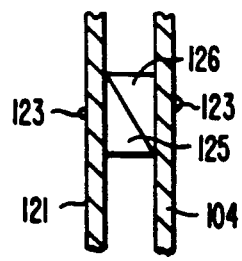
FIG._15.
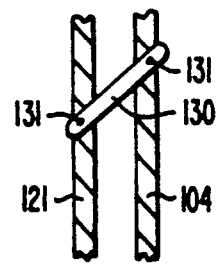
FIG._16.
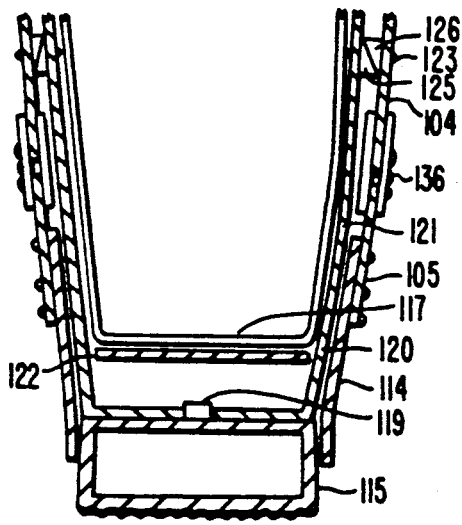
FIG._14.
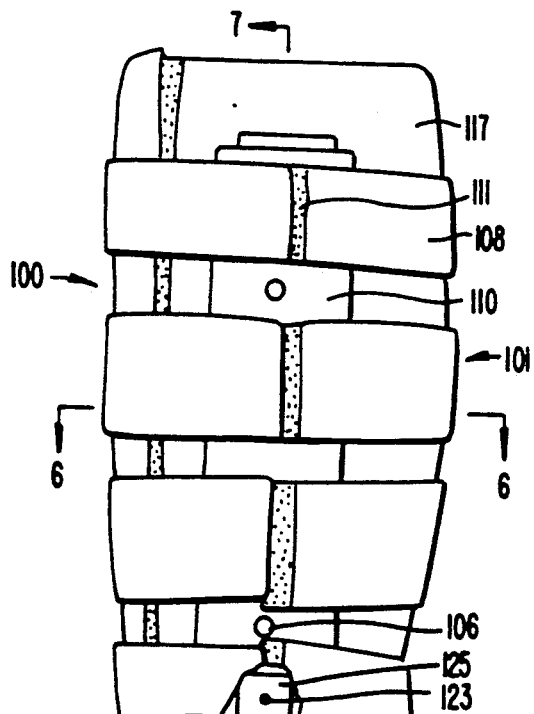
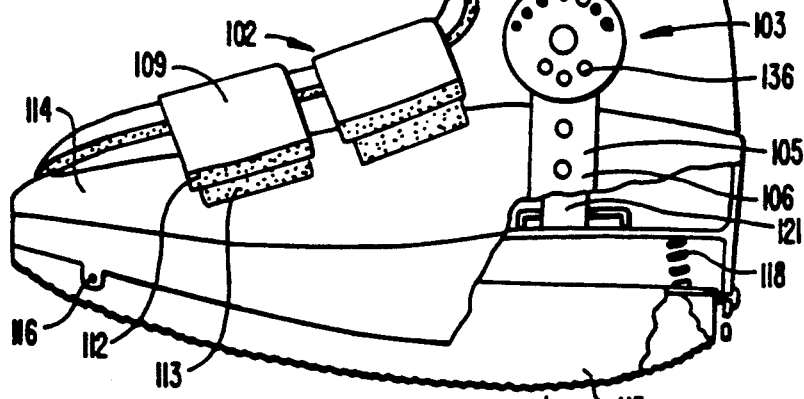
FIG._12.

WALKER BRACE

RELATED APPLICATIONS

The present application is a continuation-in-part of U.S. patent application Ser. No. 408,653 filed Sept. 18, 1989.

BACKGROUND OF THE INVENTION

The present invention relates to therapeutic and prophylactic devices, particularly to a walker brace which dynamically temporarily tightens from a snug close fit position on a patient's nested limb to stabilize the leg, ankle and foot from undesirable movement when the patient's weight is applied to the sole during contact loading with a support surface.

Various devices are known such as casts, braces, cuffs and splints that are designed to protect and stabilize the leg, ankle and foot ligaments, tendons and bones as they heal following injury or surgery. Unfortunately, these devices do not provide efficient function during the destabilizing loading phase of walking when the walker brace sole contacts the walking surface These devices tend to be either too loose on the leg, ankle and foot in which case they do not adequately stabilize the leg, ankle and foot against undesirable or abnormal movement or these devices are held too tightly, intensifying discomfort, prolonging immobility and aggravating the problem of stasis and atrophy.

SUMMARY OF THE INVENTION

It is accordingly a primary object of this invention to provide a walker brace that overcomes the deficiencies of previously known devices of the above known type.

Another object of the present invention is to provide a walker brace that dynamically temporarily tightens on a leg and foot from the snug close fit position to stabilize the leg, ankle and foot in response to loading of the lower extremity when the patient's weight is applied to the walker brace sole during the support surface contact phase of gait.

Still another object of the present invention is to provide a walker brace that can be adjusted to control the amount of tightening from the snug close fit position on the leg and foot to stabilize the ankle in response to loading when the patient's weight is applied to the sole during the support surface contact phase of gait.

Still another object of the present invention is to provide a walker brace that can progressively and differentially tighten on the leg in response to loading during the period of time that the patient's weight is applied to the sole.

BRIEF DESCRIPTION OF THE DRAWINGS

In the drawings:

FIG. 1 is a side elevation view showing a walker brace constructed according to the present invention;

FIG. 2 is a cross sectional view taken along line 2—2 of FIG. 1 showing part of the walker brace assembly secured to the leg;

FIG. 3 is a partial cross sectional view taken along line 3—3 of FIG. 1 showing part of the mechanism used to dynamically tighten the walker brace on the leg;

FIG. 4 is a side elevation view showing a walker brace constructed according to another embodiment of the present invention;

FIG. 5 is a cross sectional view taken along line 4—4 of FIG. 4 showing part of the walker brace assembly alternative embodiment secured to the leg;

FIG. 6 is a partial cross sectional view taken along line 5—5 of FIG. 4 showing part of the mechanism used to dynamically tighten the walker brace on the leg;

FIG. 7 is a reduced plan view of the lower surface of the bladder of FIG. 4;

FIG. 8 is an enlarged fragmentary cross sectional view of a portion of the bladder of FIG. 7 showing a flap valve in the lower wall of the lower chamber of the bladder with the flap in the open position;

FIG. 9 is a plan view of the valve of FIG. 8 showing the flap closing the hole in the lower wall of the lower chamber of the bladder;

FIG. 10 is an enlarged fragmentary cross sectional view of a portion of the bladder of FIG. 7 showing a flap valve between the upper and lower chambers of the bladder with the flap in the open position;

FIG. 11 is a plan view of the valve of FIG. 8 showing the flap closing the hole in the walls between the upper and lower chambers of the bladder;

FIG. 12 is a side elevation view showing a walker brace constructed according to still another embodiment of the present invention;

FIG. 13 is a cross sectional view taken along line 6—6 of FIG. 12 showing part of the walker brace assembly alternative embodiment secured to the leg;

FIG. 14 is a partial cross sectional view taken along line 7—7 of FIG. 12 showing part of the mechanism used to dynamically tighten the walker brace on the leg;

FIG. 15 is an enlarged fragmentary cross sectional view of a portion of the wedge tightening mechanism of FIG. 14 in the tightening position; and FIG. 16 is an enlarged fragmentary cross sectional view of a portion of an alternative level tightening mechanism in the tightening position.

DESCRIPTION OF THE PREFERRED EMBODIMENT

Referring to FIGS. 1-3, a walker brace 1 for a lower extremity is shown. There is particularly shown in FIG. 1 a walker brace 1 which includes a leg support assembly 2 and a foot support assembly 3 which are respectively connected to a controlled motion hinge assembly 6 at the ankle and which are located on the medial and lateral sides of the leg, ankle and foot. These components comprise a fitting assembly and are respectively adapted to engage the corresponding leg and foot above and below the ankle articulation.

On the medial side of the leg there are upper and lower arms 4 and 5 that are attached to and extend toward each other from the leg support assembly 2 and the foot support assembly 3 respectively. The upper arm 4 and the lower arm 5 terminate at the controlled motion hinge assembly 6. Upper and lower arms 4 and 5 are constructed of substantially rigid material such as plastic or metal. Hinge assembly 6 comprises identical outer and inner hinge plates 7 and 8 which are connected to the lower arm 5 by hinge assembly rivets 10 or the like. Lower arm 5 is connected to a foot support shell 28 of foot support assembly 3 with lower arm rivets 11 or the like. Upper arm 4 is pivotally connected to hinge assembly 6 by means of a hinge bolt 9 which passes through a bore in the outer hinge plate 7, the upper arm 4 and the inner hinge plate 8. Hinge assembly 6 further includes a stop pin 12 operatively coupled with the hinge assembly and the leg support assembly which can be press fit into one of a series of stop pin bores 13 in the outer hinge plate 7 and inner hinge plate 8 coincident with upper arm 4 stop pin bores 13 for controlling the forward and rearward motion of the leg support assembly relative to the hinge and foot support assemblies. Alternatively, a more complex orthotic joint can be used.

Thus, the leg support assembly 2 and foot support assembly 3 articulate at hinge bolt 9. Hinge bolt 9 forms a pivot axis which is substantially perpendicular to arms 4 and 5 and which coincides with the predominant axis through which the leg and foot articulate at the ankle.

The walker brace 1 comprises a leg support assembly 2 surrounding the leg forming a cuff and a foot support assembly 3 surrounding the foot and forming a boot. The leg support assembly 2 includes multiple anterior straps 15 which pass around the anterior aspect of the leg and are secured to the upper arm 4 by snap closures, adjustable Velcro ® strips, strap rivets 17 or the like. Multiple posterior straps 16 pass around the posterior aspect of the leg and around a substantially rigid metal tightening rod member 20 and are secured to themselves by the use of Velcro ® strip assemblies 21 or the like. The straps and tightening rod member can be located on the anterior aspect of the leg. The tightening rod member 20 can be optionally fixed to upper arm 4 to pivot relative to leg support assembly 2 near the ankle hinge assembly 6 by a tightening rod bolt 50. Also included in the upper arm 4 are tightening rod stops 26 for limiting posterior movement of the tightening rod member 20.

The posterior straps are connected with a leg strap tightening mechanism 18 for tightening against the leg when the patient's weight is applied to the sole. The leg strap tightening mechanism 18 includes the tightening rod member 20, a cable 22 which is connected to the tightening rod member 20 by a cable clamp 23 or the like and then passes around cable guide 24 secured to the upper arm 4 by a cable guide rivet 25 or the like. The cable 22 is then directed toward the foot support assembly 3. The cable 22 passes through an upper arm guide 19 and around bore guide 27 in the foot support shell 28 sidewall, through rocker bottom sole sidewall bore 40 in rocker bottom sole shell 29 to a like leg strap tightening mechanism on the lateral side of the leg. Thus, there is also formed an actuating system operatively coupled with the tightening mechanism and connected with the sole and movable relative to the sole when the patient's weight is applied to the sole.

The foot support assembly 3 includes a plastic or the like, substantially rigid, longitudinally directed, in cross section (FIG. 3) generally H-shaped, snug fitting foot support shell 28, which provides a nest for the foot connected to a sole comprising a substantially rigid, in cross-section (FIG. 3) generally U-shaped, curved rocker bottom sole shell 29 pivoted to the foot support shell 28 by rocker bottom sole pivot bolt 30. The pivot bolt 30 can be located near the forefoot and passes through a bore in the foot support shell 28 side wall and the rocker bottom sole shell 29 side wall and allows the rocker bottom sole shell 29 to pivot in an upward and downward direction about the pivot bolt 30. The foot support shell 28 may include a soft footbed insole and the rocker bottom sole shell 29 may have a skid resistant bottom covering, not shown.

The foot support assembly 3 further includes a forefoot strap 31 and an instep strap 32 respectively that pass around buckle loops 33 and 34 and can be adjusted to secure to themselves by the use of Velcro ® strip 35 and 36 assemblies, or the like. Buckle loop 33 is connected to the foot support shell 28 by a clasp 37 and a clasp rivet 38 or the like. Instep strap 32 is connected with a foot strap tightening mechanism 44 for tightening against the foot when the patient's weight is applied to the sole. The foot strap tightening mechanism 44 includes buckle loop 34 and a cable 41 which is connected to the buckle loop 34 by a cable clamp 42 or the like and is then directed in a downward direction and passes around bore guide 43 in the foot support shell 28 side wall, through rocker bottom sole side wall bore 47 in the rocker bottom sole shell 29 side wall to a like foot strap tightening mechanism on the lateral side of the foot. Thus, there is also formed an actuating system operatively coupled with the tightening mechanism and connected with the sole and movable relative to the sole when the patient's weight is applied to the sole.

A pivot stop pin 45 can be press fit into one of multiple foot support shell 28 pivot stop bores 46 near the heel in the wall of the foot support shell 28 and pass through a slot 51 in the rocker bottom sole shell 29 to control the travel distance of the rocker bottom sole shell 29 and therefore, the travel distance of the actuating system and the amount of the tightening of the straps.

The walker brace 1 can also include a soft flexible sleeve 48 wrapped around the leg and foot with a continuous overlapping front region interior of the leg support assembly 2 and foot support assembly 3. A compression spring 49 can be connected to the foot support shell 28 and rocker bottom sole shell 29 to return the rocker bottom sole shell 29 to the unweighted position when there is no contact loading with a support surface.

In use, the walker brace 1 is placed on the wearer's limb by wrapping the soft flexible sleeve 48 around the limb and situating the foot in the foot support assembly 3 and the leg in the leg support assembly 2. The posterior straps 16, forefoot strap 31 and instep strap 32 are tightened snugly around the limb in the unweighted resting position and passed around the tightening rod member 20 and buckle loops 33 and 34 respectively and secured to themselves with the Velcro ® strip assemblies 21, 35 and 36. Thus, the walker brace has a close comfortable fit in the resting unweighted position.

The stop pin 12 is press fit into a selected one of stop pin bores 13 that pass through the upper arm 4 for maintaining the selected angle of ankle dorsiflexion, such as is indicated during the early and mid phase of healing of an ankle fracture or ligament sprain. If controlled ankle motion is indicated, such as during the late phase of healing to mobilize the ankle, one or more stop pins 12 are press fit into stop pin bores 13 that do not pass through the upper arm 4, providing an end stop. The pivot stop pin 45 may be press fit into a selected one of stop pin pivot bores 46 to limit the amount of tightening of the straps.

During the period of time that the patient's weight is applied to the sole, when the walker brace rocker bottom sole shell 29 contacts the walking surface, the rocker bottom sole shell 29 pivots in an upward direction about pivot bolt 30. There is relative shortening of cable 22 and cable 41 respectively due to the increased distance between bore guide 27 in the foot support shell 28 and rocker bottom sole side wall bore 40 and bore guide 43 in the foot support shell 28 and rocker bottom sole side wall bore 47. This actuating system results in progressive and differential tightening of the multiple posterior straps 16 on the leg, increasing stability and improving venous return as the tightening rod 20 is pivoted about tightening rod bolt 50 and tightening of the instep strap 32 as the instep buckle loop 34 changes position. Thus, there is dynamic temporary tightening of the leg support assembly 2 and foot support assembly 3 from a snug close fit position on the wearer's nested limb to stabilize the leg, ankle and foot from undesirable movement.

Referring to FIGS. 4–11 in another embodiment of the present invention, a walker brace 60 is shown which includes a leg support assembly 61 and a foot support assembly 62 which are connected to a controlled motion hinge assembly 63 at the ankle and which are located on the medial and lateral sides of the leg, ankle and foot.

On the medial and lateral sides of the leg, ankle and foot, there are located substantially rigid upper and lower arms 64 and 65 respectively, that are attached to and extend toward each other from the leg support assembly 61 and the foot support assembly 62, respectively. The upper arm 64 and lower arm 65, which is attached to the foot support assembly by rivets 66 or the like, terminate and attach by rivets 99 or the like at the hinge assembly 63, which is essentially identical to the hinge assembly as shown in FIG. 1 and FIG. 3 and operates in the same manner.

The walker brace 60 comprises a leg support assembly 61 surrounding the leg, forming a cuff and a foot support assembly 62 surrounding the foot and forming a boot. The leg support assembly 61 includes multiple leg straps 68 which pass around the leg and are removably secured to a covering sleeve 67 by strap Velcro ® hook strip assemblies 69 which are glued, riveted or sewn to the multiple leg straps 68. Covering sleeve 67 is attached to each upper arm 64 by rivets 94 or the like. The covering sleeve 67 can be constructed of Velcro ® hook receiving cloth covered neoprene sheet.

The foot support assembly 62 includes multiple foot straps 70 which pass over the foot and are removably 10 secured to a foot support shell 73 by complimentary Velcro ® hook strip assemblies 71 which are glued, riveted or sewn to the multiple foot straps 70 and boot Velcro ® hook receiving strip assemblies 72 which are attached to foot support shell 73 by rivets 95 or the like.

The foot support assembly 62 includes a plastic or the like, substantially rigid, longitudinally directed, in cross-section (FIG. 6) generally H-shaped, snug fitting, foot support shell 73 connected to a sole comprising a substantially rigid, in cross-section (FIG. 6) generally U-shaped, curved rocker bottom sole shell 74 pivoted to the foot support shell 73 by rocker bottom sole pivot bolt 75 in a manner essentially identical to the assembly as shown in FIG. 1. A pivot stop pin 96 can be press fit into one of multiple foot support shell 73 pivot stop bores 97 near the heel in the wall of the foot support shell 73 and pass through a slot 98 in the rocker bottom sole shell 74 to control the travel distance of the actuating system and the amount of the tightening of the straps.

The walker brace 60 can also include a soft flexible sleeve 76 wrapped around the leg and foot with a continuous overlapping front region 77 interior of the leg support assembly 61 and foot support assembly 62 in a manner essentially identical to the assembly as shown in FIGS. 1–3. A compression spring 78 is connected to the foot support shell 73 and rocker bottom sole shell 74. The compression spring 78 returns the rocker bottom sole shell 74 to the unweighted position when there is no contact loading with a support surface.

As shown in FIGS. 4–7, located between the foot support shell 73 and the rocker bottom sole shell 74 and between the soft flexible sleeve 76 and the multiple leg straps 68 is a conforming inflatable bladder 80. Inflatable bladder 80 includes lower chamber 81 located between the foot support shell 73 and the rocker bottom sole shell 74 and an upper chamber 82 which lies between the multiple leg straps 68 and the soft flexible sleeve 76. The inflatable bladder 80 comprises a lower wall 83 and an upper wall 84, walls 83 and 84 defining the fluid fillable bladder 80. Allowance is made in the design and construction of the bladder 80 for the location of compression spring 78.

Bladder 80 may contain air, Freon ®, gel or liquid or the like. When air is the selected fluid, the lower chamber 81 lower wall 83 as shown in FIGS. 8–9 includes a valve such as a butterfly valve or a flap valve 86, which includes a hole 87 in the lower wall 83 of the bladder 80 and a flap 88 hinged to the lower wall 83 for movement into and out of closing relationship to hole 87. As shown in FIGS. 10–11, the lower chamber 81 overlaps and is connected to the upper chamber 82 by a valve 89 which includes a hole 90 between the lower wall 83 of the upper chamber 82 and the upper wall 84 of the lower chamber 81. A flap 91 is hinged to the lower wall 83 of the upper chamber 82 and includes a hole 92 which allows a difference in the rate of flow of air between the upper chamber 82 and the lower chamber 81 when the flap 91 is in the open or closed position.

In use, the walker brace 60 is placed on the wearer's limb by situating the foot in the foot support assembly 62 and the leg in the leg support assembly 61. The soft flexible sleeve 76 is wrapped around the limb. The foot straps 70 are placed on the limb, tightened snugly and secured to the Velcro ® hook receiving strip assemblies 72 on the foot support shell 73 in the rested, unweighted position. The multiple leg straps 68 are placed over the bladder and around the limb in the rested, unweighted position, tightened snugly and secured to the upper arm covering sleeve 67 with the Velcro ® hook strip assemblies 69.

During the period of time that the patient's weight is applied to the sole, when the walker brace rocker bottom sole shell 74 contacts the walking surface, the rocker bottom sole shell 74 pivots in an upward direction about pivot bolt 75. There is a decrease in distance between the upper surface of the rocker bottom sole shell 74 and the lower surface of the foot support shell 73 reducing the volume of bladder 80 lower chamber 81 forcing a portion of the contained air into upper chamber 82 through opened valve 89. This actuating system results in tightening of the multiple leg straps 68 on the leg, due to the pressure of the inflated bladder 80 upper chamber 82 against the multiple leg straps 68 and the soft flexible sleeve 76 and leg, increasing leg, ankle and foot stability and improving venous return.

During the period of time that the patient's weight is not applied to the sole, when the walker brace 60 rocker bottom sole shell 74 does not contact the walking surface, compression spring 78 returns the rocker bottom sole shell 74 to the unweighted position. Thus, the distance between the upper surface of the rocker bottom sole shell 74 and the lower surface of the foot support shell 73 is increased. This results in an increase in the volume of air in bladder 80 lower chamber 81 as valve 86 opens allowing ambient air to enter lower chamber 81 and valve 89 allows a portion of the contained air in the upper chamber 82 to flow through the hole 92 in flap 91 of valve 89 into the lower chamber 81 loosening the leg straps 68 on the leg. Thus, there is a temporary dynamic tightening of the leg support assembly from a snug close fit on the wearer's nested limb which stabilizes the limb from undesirable movement. If oil is used as the fluid in bladder 80, there is no flap in the valve 89. If Freon ® is used, there is no valve 86.

Referring to FIGS. 11–16 in still another embodiment of the present invention, a walker brace 100 is shown which includes a leg support assembly 101 and a foot support assembly 102 which are connected to a controlled motion hinge assembly 103 at the ankle and which are located on the medial and lateral sides of the leg, ankle and foot.

On the medial and lateral sides of the leg, ankle and foot are located substantially rigid upper and lower arms 104 and 105 respectively, that are attached to and extend toward each other from the leg support assembly 101 and the foot support assembly 102. The lower arm 105 is attached to the foot support assembly by rivets 106 or the like and the upper arm 104 and lower arm 105 terminate and attach by rivets 136 or the like at the controlled motion hinge assembly 103 which is essentially identical to the hinge assembly as shown in FIG. 1 and FIG. 3 and operates in the same manner.

The leg support assembly 101 includes multiple leg straps 108 which pass around the leg and are removably secured on one or both sides of the leg to a covering sleeve 110, which is attached to each upper arm 104 by rivets 106 or the like, in a manner identical to that shown in FIGS. 4–6. The covering sleeve 110 is constructed of a Velcro ® hook receiving material. The multiple leg straps 108 include Velcro ® hook strip assemblies 111 which are sewn to the straps 108.

The foot support assembly 102 includes multiple foot straps 109 which pass over the foot and are removably secured to the foot support shell 114 by complimentary foot strap Velcro ® hook strip assemblies 112 sewn to the foot straps 109 and Velcro ® hook receiving strip assemblies 113 glued or riveted or the like to the foot support shell 114 in a manner similar to that shown in FIG. 4.

The foot support assembly 102 includes a substantially rigid, longitudinally directed, in cross section (FIG. 14) generally H-shaped foot support shell 114 connected to a sole comprising a substantially rigid, in cross section (FIG. 14) generally U-shaped, curved rocker bottom sole shell 115 pivoted to the foot support shell 4 by rocker sole bottom pivot bolt 116 in a manner essentially identical to the assembly as shown in FIG. 1. The walker brace 100 can also include a soft flexible sleeve 117 similar to the sleeve 76 as shown in FIGS. 4–6. A compression spring 118 is connected to the foot support shell 114 and rocker bottom sole shell 115 to return the rocker bottom sole shell 115 to the unweighted position when there is no contact loading with a support surface.

A generally U-shaped slightly flexible tightening bar 120 constructed of metal or plastic or the like is slidably connected by a guide 119 to the upper surface of the rocker bottom sole shell 115. The tightening bar 120 has tightening arms 121 which extend in an upward direction through a slot 122 in the foot support shell 114 along the inner side of each lower arm 105 on the medial and lateral sides of the leg. Each tightening arm 121 then extends in an upward direction on the inner side of each upper arm 104. The tightening bar 120 can slide on the upper surface of the rocker bottom sole shell 115 to accommodate the angular movement of the leg support assembly 101 relative to the foot support assembly 102. Multiple complimentary shaped wedge assemblies 125 and 126 are attached at several levels to the outer surface of each tightening arm 121 and the inner surface of each upper arm 104 respectively by rivets 123 or the like. Alternatively, as shown in FIG. 16, lever arms 130 can be pivoted by pins 131 or the like between each side of the tightening arms 121 and the upper arms 104 to increase or decrease the distance between the arms as they move relative to each other.

During the period of time that the patient's weight is applied to the sole, when the walker brace rocker bottom sole shell 115 contacts the walking surface, the rocker bottom sole shell 115 pivots in an upward direction about pivot bolt 116. Thus, the tightening bar 120 and tightening arms 121 move in an upward direction relative to each upper arm 104 moving the complimentary shaped wedge assemblies 125 and 126 against each other increasing the distance between each tightening arm 121 and each upper arm 104. This actuating system results in tightening of the multiple leg straps 108 on the leg due to the pressure of each tightening arm 121 against each upper arm 104, the soft flexible sleeve 117 and leg and the upper arm 104 against the multiple leg straps 108 increasing stability and improving venous return.

During the period of time that the patient's weight is not applied to the sole, when the walker brace 80 rocker bottom sole shell 115 does not contact the walking surface, compression spring 118 returns the rocker bottom sole shell 115 to the unweighted position. Each tightening bar 120 and tightening arm 121 moves in a downward direction relative to each upper arm 104 moving the complimentary shaped wedge assemblies 125 and 126 away from each other decreasing the distance between each tightening arm 121 and upper arm 104 loosening the multiple leg straps 108 on the leg. Thus, there is a temporary dynamic tightening of the leg support assembly from the snug close fit on the wearer's nested limb which stabilizes the limb from undesirable movement.

Details have been disclosed to illustrate the invention in a preferred embodiment of which adaptations and modifications within the spirit and scope of the invention will occur to those skilled in the Art. The scope of the invention is limited only by the following claims.

What is claimed is:

1. A walker brace for stabilizing a patient's ankle comprising:
   a substantially rigid foot support assembly for receiving a patient's foot including a sole and including at least one strap member for tightening against the foot;
   a substantially rigid leg support assembly for receiving the patient's corresponding leg and including at least one strap member for tightening against the leg;
   a controlled motion hinge assembly connecting the foot support assembly to the leg support assembly;
   an actuating system coupled with the sole and movable relative to the sole in response to the application of the patient's weight to the sole; and
   a tightening mechanism operatively coupled with the actuating system and at least one strap member for increasing the tightness of the strap member on the foot and/or leg in response to movement of the actuating system relative to the sole as a result of the application of the patient's weight to the sole.

2. A walker brace according to claim 1 further comprising at least one stop pin operative coupled with the hinge assembly and the leg support assembly for controlling the forward and rearward motion of the leg support assembly relative to the hinge assembly.

3. A walker brace according to claim 1, further comprising a tightening mechanism that includes a fluid filled bladder operatively coupled with the actuating system and the strap member.

4. A walker brace according to claim 3 further comprising an assembly for adjusting the tightness of the strap member.

5. A walker brace according to claim 4 further comprising a tightening mechanism operatively coupled with the actuating system for temporarily increasing the tightness of the strap member during the period of time that the patient's weight is applied to the sole.

6. A walker brace according to claim 4 further comprising an actuating system movable between an unweighted position and a weighted position, and a return member operatively connected with the sole and the actuating system for returning of the actuating system to the unweighted position.

7. A walker brace according to claim 6 further comprising a spring return member.

8. A walker brace according to claim 6 further comprising a stop member operatively coupled with the sole and the actuating system for controlling the travel distance of the actuating system.

9. A walker brace according to claim 1 further comprising a tightening mechanism that includes a bar operatively coupled with the actuating system and the strap member.

10. A walker brace according to claim 9 further comprising an assembly for adjusting the tightness of the strap member.

11. A walker brace according to claim 9 further comprising a tightening mechanism operatively coupled with the actuating system for temporarily increasing the tightness of the strap member during the period of time that the patient's weight is applied to the sole.

12. A walker brace according to claim 9 further comprising an actuating system movable between an unweighted position and a weighted position, and a return member operatively connected with the sole and the actuating system for returning of the actuating system to the unweighted position.

13. A walker brace according to claim 12 further comprising a spring return member.

14. A walker brace according to claim 9 further comprising a stop member operatively coupled with the sole and the actuating system for controlling the travel distance of the actuating system.

15. A walker brace for immobilizing an ankle joint between a patient'foot and leg and for increasing the tightness with which the brace is applied when the patient applies his weight to the brace, the brace comprising:

a boot including a substantially rigid support surface for the foot and a foot strap adapted to be placed over an instep portion of the foot;

a substantially rigid cuff substantially immovably secured to the boot, extending from the boot in a general upward direction, and including a leg strap for placement about the leg;

a sole mounted to the boot, formed and positioned so that the sole engages a ground surface when the patient applies his weight to the support surface of the boot and means permitting movement of the sole relative to the rigid support surface when the patient applies his weight to the boot and the sole; and cable means having ends attached to ends of the foot strap and the leg strap and an intermediate portion in simultaneous engagement with a section of the boot and the sole so that relative movement of the sole under the weight applied thereto by the patient draws the foot strap and the leg strap against the foot and the leg, respectively, with an increased force to thereby temporarily increase the tightness with which the brace engages the foot and the leg in response to and while the patient's weight is applied to the sole.

16. A walker brace according to claim 15, including means for limiting the extent to which the sole can move relative to the boot when the patient's weight is applied to the sole.

17. A walker brace according to claim 16 wherein the movement limiting means includes means for adjusting the amount of relative movement of the sole.

18. A walker brace according to claim 16 including means between the boot and the cuff for varying the angular inclination therebetween.

* * * * *